United States Patent
Belden et al.

(10) Patent No.: US 6,501,992 B1
(45) Date of Patent: Dec. 31, 2002

(54) RADIOPAQUE MARKING OF LEAD ELECTRODE ZONE IN A CONTINUOUS CONDUCTOR CONSTRUCTION

(75) Inventors: Elisabeth L. Belden, Maple Grove, MN (US); Gregory A. Boser, Richfield, MN (US); Michael R. Dollimer, Burnsville, MN (US); Mary M. Morris, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 58 days.

(21) Appl. No.: 09/690,163

(22) Filed: Oct. 17, 2000

(51) Int. Cl.[7] .................................................. A61N 1/05
(52) U.S. Cl. ....................................................... 607/122
(58) Field of Search ................................. 600/373, 374, 600/424, 434; 607/119, 122, 127

(56) References Cited

U.S. PATENT DOCUMENTS

| | | | |
|---|---|---|---|
| 4,481,953 A | | 11/1984 | Gold et al. |
| 4,617,932 A | | 10/1986 | Kornberg |
| 4,693,703 A | * | 9/1987 | Rosenberg .................... 604/49 |
| 4,932,407 A | | 6/1990 | Williams |
| 5,042,143 A | | 8/1991 | Holleman et al. |
| 5,078,726 A | | 1/1992 | Kreamer |
| 5,090,422 A | | 2/1992 | Dahl et al. |
| 5,265,623 A | | 11/1993 | Kroll et al. |
| 5,405,374 A | | 4/1995 | Stein |
| 5,423,763 A | * | 6/1995 | Helland et al. .............. 604/174 |
| 5,439,485 A | | 8/1995 | Mar et al. |
| 5,473,812 A | * | 12/1995 | Morris et al. .................. 29/825 |
| 5,728,149 A | | 3/1998 | Laske et al. |
| 5,871,530 A | * | 2/1999 | Williams et al. ............. 607/122 |
| 5,948,015 A | | 9/1999 | Hess et al. ................... 607/127 |
| 5,957,961 A | * | 9/1999 | Maguire et al. ............... 607/99 |
| 5,957,966 A | | 9/1999 | Schroeppel et al. ......... 607/122 |
| 5,964,795 A | | 10/1999 | McVenes et al. ............ 607/122 |
| 5,984,877 A | * | 11/1999 | Fleischhacker, Jr. ......... 600/585 |
| 6,168,570 B1 | * | 1/2001 | Ferrera ......................... 600/585 |

FOREIGN PATENT DOCUMENTS

WO     WO 00/01441     1/2000

* cited by examiner

*Primary Examiner*—Jeffrey R. Jastrzab
*Assistant Examiner*—Frances P. Oropeza
(74) *Attorney, Agent, or Firm*—Girma Wolde-Michael

(57) ABSTRACT

A cardiac transvenous defibrillation lead has a continuous coil conductor within a layer of insulation. A portion of the coil conductor is exposed as a defibrillation electrode. In order to enhance fluoroscopic visualization of the exposed electrode during implant, the end of the exposed electrode is marked with a radiopaque element. The element may be in the form of an adhesive filled with radiopaque material that is used to backfill under the layer of insulation. Alternatively, a tube made of radiopaque material may be installed between the layer of insulation and the coil conductor.

3 Claims, 6 Drawing Sheets

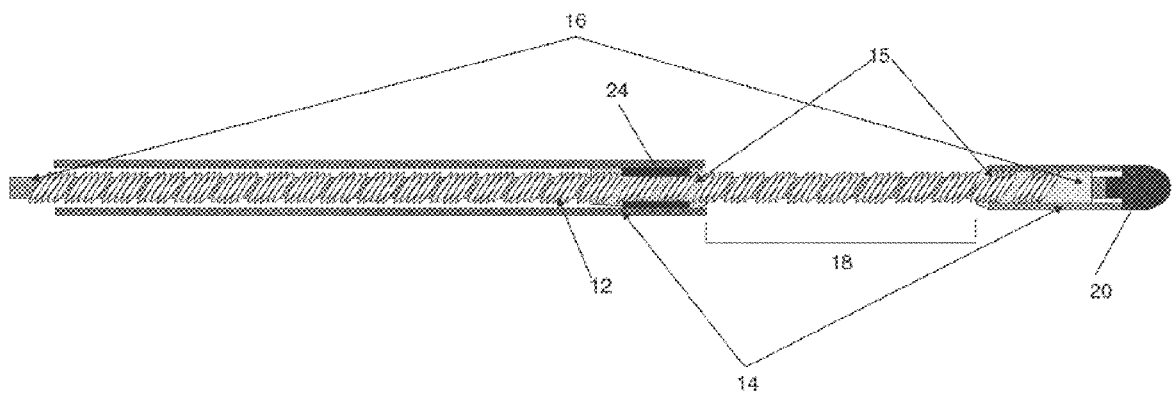
FIGURE 2. A.

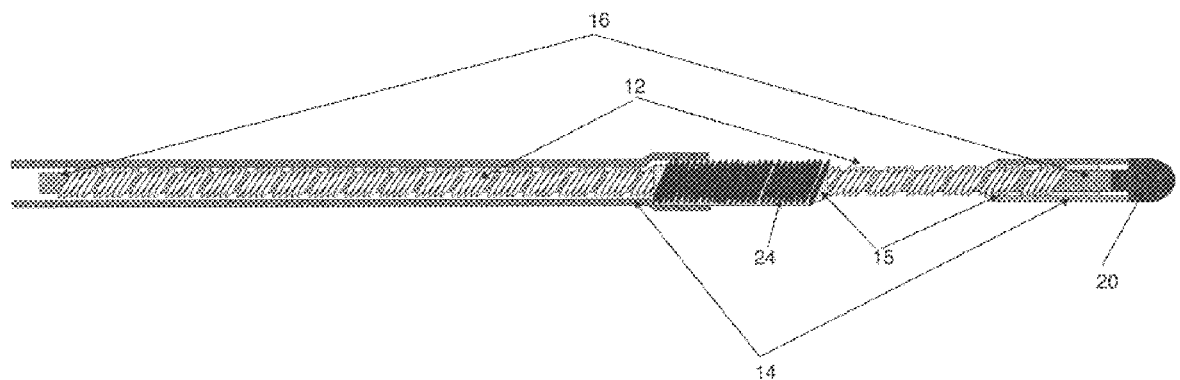
FIGURE 2.B.

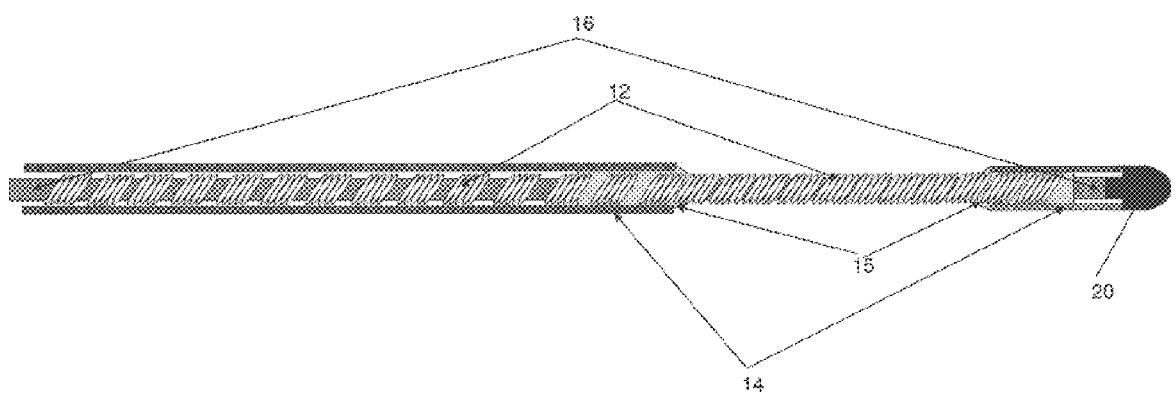
FIGURE 4.A.

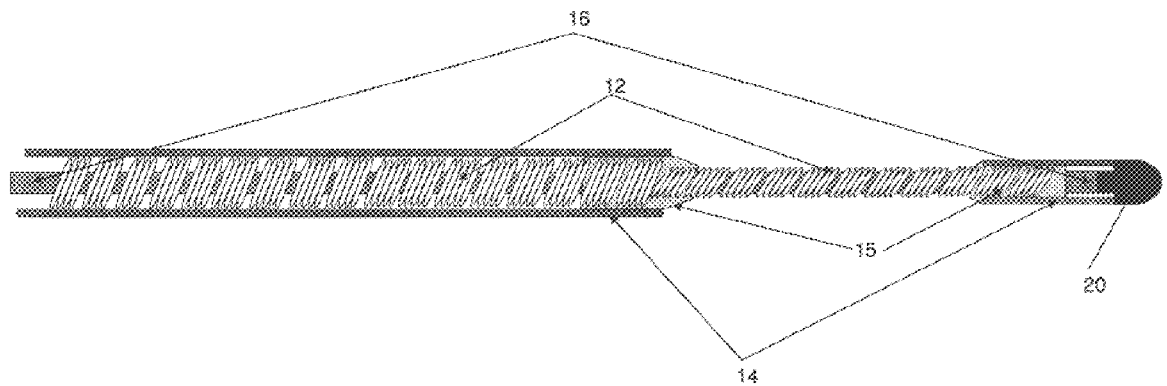
FIGURE 4. B.

RADIOPAQUE MARKING OF LEAD ELECTRODE ZONE IN A CONTINUOUS CONDUCTOR CONSTRUCTION

FIELD OF THE INVENTION

This invention generally relates to implantable medical devices. Specifically, this invention relates to implantable electrode leads and implantable stimulators, and more particularly to implantable electrode leads as implemented in implantable defibrillators and similar pacing medical devices.

BACKGROUND OF THE INVENTION

Implantable ventricular defibrillators, including multi-programmable, pacemaker/cardioverter/defibrillator ("PCD"), typically employ epicardial or subcutaneous patch electrodes, alone, or in conjunction with one or more transvenously introduced endocardial leads with one or more electrodes disposed within a heart chamber or blood vessel. Ventricular defibrillation is typically effected with at least one electrode extending along an endocardial lead body disposed within the right ventricle and one or more additional defibrillation electrodes disposed outside the right ventricle to provide two or more defibrillation current pathways through the chamber of the heart to be defibrillated. Other endocardial defibrillation leads for transvenously introducing and positioning defibrillation electrodes into the right atrium and/or superior vena cava, the coronary sinus, the right outflow track or other locations in proximity to the heart have been disclosed in the prior art, including commonly assigned U.S. Pat. No. 4,932,407 to Williams.

The typical endocardial lead defibrillation electrode is configured as an elongated wire of high conductivity that is spirally space wound or close wound about the lead body for a length appropriate for the intended use. The spacing of the coil turns retains flexibility of the lead body along the length of the electrode and distributes the electrode surface area along the length thereof. The wire cross-section is typically circular, as shown in U.S. Pat. No. 5,042,143 to Holleman et al., or rectangular, as shown in U.S. Pat. No. 4,481,953 to Gold et al., U.S. Pat. No. 5,090,422 to Dahl et al., and U.S. Pat. No. 5,265,653 to Kroll et al., although other wire configurations, e.g. the wrapped coils of U.S. Pat. No. 5,439,485 to Mar et al., have also been proposed. The coiled wire electrode may be formed of a single wire or in a multi-filar configuration of interlaced wires. The coiled wire turns are typically partially embedded into the underlying lead body insulation to mechanically stabilize the exposed coil turns at the distal portion and direct the defibrillation current outward of the lead body.

When one continuous coil performs as the conductor and the electrode, the exposed electrode portion cannot be distinguished from the insulated portion when the lead is implanted because the entire length of the lead is of equal radiopacity. Thus, it becomes difficult to see with precision where the exposed electrode portion of the coil resides within the heart—the right ventricle, atrium, superior vena cava, etc. One approach has been to ascertain in advance the length of the exposed electrode portion and based on that information estimate the position of the electrode. However, if the anatomy creates a curvilinear path, difficulty is encountered in making the estimate without multiple fluoroscopic views.

Accordingly, there is a need to accurately determine the position of the electrode to strategically place the lead in the heart within a zone, provide effective delivery of electrical charges at the zone and enable selective positioning of the electrode.

SUMMARY OF THE INVENTION

The present invention is directed towards defibrillation leads and defibrillation lead systems that have a continuous coil construction within an insulation layer and an exposed electrode portion proximate the distal end of the lead body. The wire from which the coil is made will typically have an outer layer of platinum or platinum iridium to provide an effective electrode surface that is bio-stable and biocompatible. In particular, the present invention seeks to address the problem associated with such leads of determining with precision where the exposed electrode portion resides within the heart when the lead is being implanted. In general, the present invention addresses the problem by marking the electrode with additional radiopacity. In one approach, an adhesive filled with radiopaque material is used to backfill under the distal end of the outer insulation at the proximal end of the exposed electrode portion. Alternatively, a band of radiopaque material can be placed at either end of the exposed electrode portion. The result obtained is that enhanced fluoroscopic visualization of the electrode portion of the coil lead is provided, and the precise location where the exposed electrode resides within the heart is more readily ascertained.

BRIEF DESCRIPTION OF THE DRAWINGS

The advantages and features of the present invention will become better understood from the following detailed description of illustrative embodiments thereof when considered in conjunction with the drawing figures wherein:

FIGS. 2A and B depict section views of the distal end of a coil defibrillation lead according to a second embodiment of the present invention, and wherein a band of radiopaque material is installed at the proximal end of the exposed electrode portion of the lead.

FIGS. 4A and 4B depict (a) section views of the distal end of a coil defibrillation lead according to a fourth embodiment of the present invention wherein the diameter and/or cross-section of coil conductor 12 can be varied in the exposed segment forming the active electrode.

DETAILED DESCRIPTION OF ILLUSTRATIVE EMBODIMENTS

Figure 1:
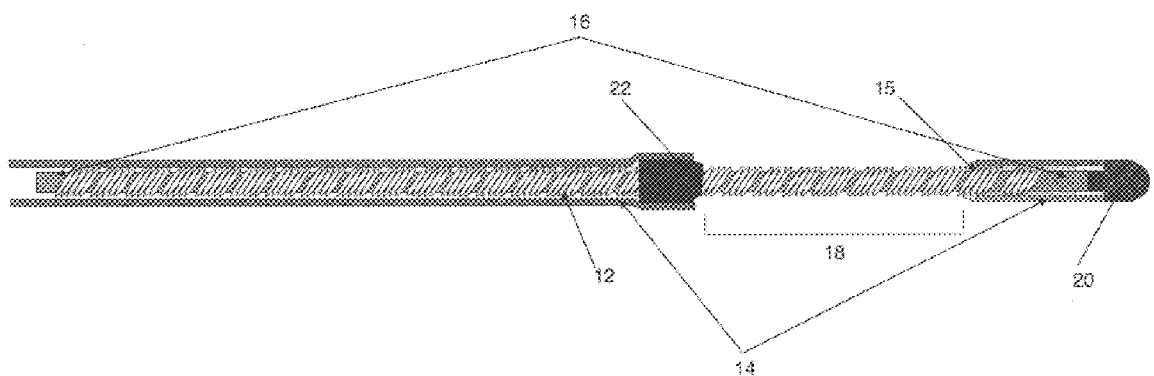
FIG. 1 is a section view of the distal end of a coil defibrillation lead according to a first embodiment of the present invention and wherein an adhesive filled with radiopaque material is used to backfill under the insulation layer at the proximal end of the exposed electrode portion of the lead.

FIG. 1 shows the distal end of a lead 10 in accordance with the present invention. Lead 10 is suitable for use as a transvenous right ventricular defibrillation lead. The cross-section view of FIG. 1 shows that lead 10 has an elongated lead body comprising a coiled wire conductor 12 within an insulating layer 14. The coil conductor 12 is preferably a helically-wound coil that defines a hollow center with an axial bore. Outer insulation 14 terminates at a predetermined distance to form the exposed electrode portion 18. Inner assembly 16 could be a tubing to provide a lumen for stylet passage or it could be an insulated cable conductor. The tip of lead 20 could be an insulated termination of the lead body or an electrode. Clearly, such a structure will need an inner tubing under the coil to prevent fluid leakage into the core of the lead body through the exposed portion of the coil, to provide support for exposed portion of the coil, and as a surface to carry the radiopaque marking for the coil. A body 22 of adhesive material is positioned as a backfill under the insulation layer 14 at the proximal edge of the exposed electrode 18. The adhesive contains radiopaque material such as tantalum powder. The additional radiopacity will blend with the coils in the backfill region and show as a larger diameter fillet. The appearance of the larger diameter will serve to assist in determining where the exposed electrode resides within the heart as the lead is being placed during implant.

In FIG. 2A, a second embodiment is shown. In this embodiment, a tube 24 of radiopaque material is installed between the coil conductor 12 and the inside surface of the insulation layer 14. The tube may be a ring made from platinum iridium or a polymer tubing made radiopaque using barium sulfate as a filler. As shown, the tube 24 is placed along the lead at a location adjacent the exposed electrode 18. A preferred embodiment employs a platinum coil 24 (Pt/IR spring) as a marker band. The marker coil is partially contained beneath insulation 14 and extends over the exposed electrode 18 (in order to strain-relieve the transition zone) as shown in FIG. 2B. One aspect of the invention enables this structure to be adaptable to various lengths that may be required for enhanced radiopacity. The structure further provides a strain relief at the transition points between the layers of structure elements of lead 10 and segments of radiopaque material.

Figure 3:
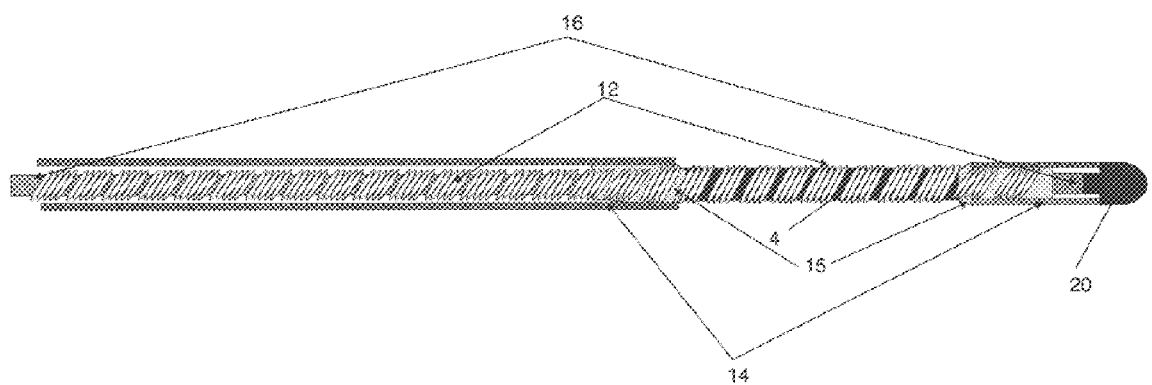
FIG. 3 depicts a section view of the distal end of a coil defibrillation lead according to a third embodiment of the present invention wherein the radiopaque marker element is extended beneath the entire length of the exposed portion of the coil.

Referring to FIG. 3, an additional layer of tubing 4 or a portion of the inner assembly tubing in this zone that is meant to be radiopaque with a filler such as barium sulphate can be installed beneath the coil along the entire length of the exposed section of coiled conductor 12. Similarly, a backfill of adhesive filled with radiopaque powder can be applied along the entire length of the exposed coil conductor 12 between coil filars. It should be noted that adhesive backfill 14 could be filled with any radiopaque element in the form of powder that is biostable.

Further, the diameter and/or cross-section of coil conductor 12 can be varied in the exposed segment forming the active electrode. FIGS. 4A and 4B depict this embodiment of the present invention. Specifically, FIG. 4A shows a reduced pitch over the length of exposed segment of coil conductor 12. Similarly, FIG. 4B shows a diminished section over the length of exposed coil conductor 12. In both embodiments, adhesive backfill 15 is implemented to isolate the exposed section of lead 10 from the unexposed sections.

In a further aspect of the invention, the radiopaque marking would also be useful for a catheter of similar construction. In this type of application, preferably a portion of reinforcing metal braid in the wall of a catheter is exposed as an electrode.

Although only a distal portion of the defibrillation lead 10 is shown in the drawing figures, the remaining structure of the lead, as well as modifications and variations on the structure shown, is known to those of skill in the art. Further details of a suitable overall lead configuration may be obtained, for example, from the disclosures of U.S. Pat. Nos. 5,405,374 and 5,728,149, both of which are hereby incorporated by reference.

While the present invention has been described with reference to particular illustrative embodiments for purposes of explanation and illustration, modifications and variations may be undertaken to produce lead structures that differ from those shown and discussed herein without departing from the concepts of the invention. For example, in the embodiment of FIG. 1, a radiopaque adhesive backfill may also be placed adjacent the distal end of the exposed electrode. As such, the embodiments disclosed herein are to be considered exemplary rather than limiting with regard to the scope of the present invention.

What is claimed is:

1. A transvenous lead, comprising:
   a continuous coil conductor having a proximal portion and a distal portion, the proximal portion covered with a layer of insulation and the distal portion exposed as an electrode, the proximal and distal portions having substantially equivalent radiopaque characteristics; and
   a tube of radiopaque material, including a Pt/IR spring, installed as a marker over the continuous coil conductor at a location adjacent to a proximal end of the exposed distal portion of the coil conductor; wherein
   the Pt/IR spring extends from under the layer of insulation, adjacent to the proximal end of the exposed distal portion of the coil conductor, distally, over a portion of the exposed distal portion of the coil conductor.

2. A transvenous lead, comprising:
   a continuous coil conductor having a proximal portion and a distal portion, the proximal portion covered with a layer of insulation and the distal portion exposed as an electrode, the proximal and distal portions having substantially equivalent radiopaque characteristics; and
   a body of adhesive filled with a radiopaque material positioned as a marker around the continuous coil conductor at a location adjacent to a proximal end of the exposed distal portion of the coil conductor; wherein
   the body of adhesive extends from under the layer of insulation, adjacent to the proximal end of the exposed distal portion of the coil conductor, distally, over a portion of the exposed distal portion of the coil conductor.

3. A transvenous lead, comprising:
   a continuous coil conductor having a proximal portion and a distal portion, the proximal portion covered with a layer of insulation and the distal portion exposed as an electrode, the proximal and distal portions having substantially equivalent radiopaque characteristics; and
   a tube of radiopaque material, including a polymer filled with barium sulfate, installed as a marker over the continuous coil conductor at a location adjacent to a proximal end of the exposed distal portion of the coil conductor; wherein
   the tube of radiopaque material extends from under the layer of insulation, adjacent to the proximal end of the exposed distal portion of the coil conductor, distally, over a portion of the exposed distal portion of the coil conductor.

\* \* \* \* \*